United States Patent [19]

Ruano

[11] Patent Number: 5,427,911
[45] Date of Patent: Jun. 27, 1995

[54] COUPLED AMPLIFICATION AND SEQUENCING OF DNA

[75] Inventor: Gualberto Ruano, New Haven, Conn.

[73] Assignee: Yale University, New Haven, Conn.

[21] Appl. No.: 98,748

[22] Filed: Jul. 28, 1993

Related U.S. Application Data

[63] Continuation of Ser. No. 516,499, May 1, 1990, abandoned.

[51] Int. Cl.⁶ .................. C12Q 1/68; C12P 19/34; C07H 21/04
[52] U.S. Cl. ..................... 435/6; 435/91.2; 536/24.33
[58] Field of Search ................. 435/6, 91.2; 536/24.33

[56] References Cited

U.S. PATENT DOCUMENTS 4,683,195  7/1987  Mullis et al. .................... 435/6

OTHER PUBLICATIONS

K. B. Mullis and F. A. Foloona, "Specific Synthesis of DNA *In Vitro* via a Polymeric–Catalyzed Chain Reaction," *Methods in Enzymology*, 155, 335–350.
U. B. Gyllensten and H. A. Erlich, "Generation of Single-Stranded DNA by the Polymerase Chain Reaction and Its Application to Direct Sequencing of the HLA–DQA Locus," *PNAS USA*, 85, 7652–7656 (1988).
Ruano and Kidd, Proc. Natl. Acad. Sci. USA, Apr. 1991, v. 88, 2815–19.
Ruano and Kidd, Nucleic Acids Res, v. 19, 1991, pp. 6877–6882.
Carethers et al, BioTechniques, vol. 7, May 1989, pp. 494–498.
Nurakawa et al, DNA, v. 7, 1988, pp. 287–295.
Sarger et al, Proc. Natl. Acad. Sci USA, vol. 74, No. 12, Dec. 1977, pp. 5463–5467.

*Primary Examiner*—Mindy B. Fleisher
*Attorney, Agent, or Firm*—Eugene Moroz; Dorothy R. Auth

[57] ABSTRACT

A process for sequencing DNA segments having complementary strands comprising (a) synthesizing simultaneously truncated products and full-length products starting from both 3' ends of the complementary strands of the DNA segment, which serves as a template, by introducing specific oligonucleotide primers annealing to the 3' ends of both complementary strands of the DNA segment, a deoxyribonucleotide elongator for each of adenine, guanine, cytosine and thymine, a thermally stable DNA polymerase and a terminator for each of adenine, guanine, cytosine and thymine, (b) thermally cycling step (a), (c) separating out the resultant truncated products and full length products according to size, and (d) selectively detecting all truncated products and full length products according to size, and (e) selectively detecting all truncated products and full-length products generated from a given strand of template.

21 Claims, 5 Drawing Sheets

COUPLED AMPLIFICATION AND SEQUENCING (CAS)

COUPLED AMPLIFICATION AND SEQUENCING OF DNA

GOVERNMENT RIGHTS

This invention was made with United States government support under Grant GM40883-02 from the National Institute of Health and the Department of Health. The United States Government has certain rights in this invention.

This application is a Continuation of application Ser. No. 07/516,499, filed May 1, 1990 now abandoned.

BACKGROUND OF THE INVENTION

1. Field of the Invention

The present invention concerns a method to sequence a genomic DNA, a cloned DNA, a single stranded DNA or an oligonucleotide. One embodiment of the inventive process couples amplification of genomic DNA via the polymerase chain reaction (PCR) with DNA sequencing via dideoxynucleotide chain termination.

2. Background of the Invention

The polymerase chain reaction is described in Mullis and Faloona, 1987, *Methods Enzymol.*, 155, 335 and in U.S. Pat. Nos. 4,683,195 and 4,683,2.02. The entire contents of U.S. Pat. Nos. 4,683,195 and 4,683,202 are incorporated by reference herein.

DNA sequencing via dideoxynucleotide chain termination is described in Sanger et al, 1977, *Proc. Natl. Acad. Sci. USA*, 74, 5463.

Direct sequencing of PCR products has proven difficult because of reannealing of the complementary strands, which often disturbs primer extension along the template. Although asymmetric PCR and M13 cloning of PCR products produce single stranded templates suitable for sequencing, these methods require multiple preparative steps.

Many prior protocols require nested primers for the sequencing steps.

Asymmetric PCR (Gyllenstein and Erlich, 1988, *Proc. Natl. Acad. Sci. USA*, 85, 7652) is a procedure for sequencing PCR products. Asymmetric PCR generates an excess of one DNA strand which is to be sequenced. Considerable empirical testing for every template is required to obtain sequence data from both strands for confirmation.

Most heretofore sequencing methods rely on a single primer extension reaction With chain-terminating dideoxynucleotides.

SUMMARY OF THE INVENTION

It is an object of the invention to provide methods for sequencing genomic DNA, single stranded DNA and oligonucleotides.

It is another object of the present invention to sequence cloned DNA.

It is a further object of the present invention to conduct the sequencing of genomic DNA, single stranded DNA or oligonucleotides in such a manner that amplification leads directly to sequencing.

It is another object of the present invention to detect genetic diseases and tumors.

It is a further object of the present invention to determine paternity.

It is still another object of the invention to identify individuals and animals on the basis of DNA sequence.

The above objects, as well as other objects, aims and advantages are satisfied by the present invention.

The present invention concerns a process for sequencing a genomic DNA of less than 2 kb, a single stranded DNA of less than 2 kb or an oligonucleotide of less than 100 nucleotides comprising
  (a) amplifying in vitro the genomic DNA, the single stranded DNA or the oligonucleotide to obtain at least 10 femtomoles of the genomic DNA, the single stranded DNA of the oligonucleotide, whereby to form a template,
  (b) synthesizing simultaneously truncated strands from both ends of the template by introducing dideoxyribonucleotide, hereinafter referred to as a dideoxynucleotide terminator for each of ,the four bases adenine, guanine, cytosine and thymine and introducing a label or labels specific for either or both of the 5' ends of the synthesized strands,
  (c) thermally cycling step (b) to provide a sufficiently readable signal and
  (d) separating out the resultant molecules according to size.

The present invention also relates to a process for sequencing a cloned DNA comprising
  (a) synthesizing simultaneously truncated strands from both ends of a vector delimiting and containing the cloned DNA which acts as a template by introducing deoxyribonucleotide, hereinafter referred to as deoxynucleotide elongators for each of adenine, guanine, cytosine and thymine, a thermally stable enzyme, a dideoxynucleotide terminator for each of the four bases adenine, guanine, cytosine and thymine and a specific label or labels for either or both of the 5' ends of the synthesized strands,
  (b) thermally cycling step (a) to provide a sufficiently readable signal and
  (c) separating out the resultant molecules according to size.

The present invention is also directed to a process (hereinafter referred to as the "aliquot process") for sequencing a genomic DNA of less than 2 kb, a single stranded DNA of less than 2 kb or an oligonucleotide of less than 100 nucleotides comprising
  (a) amplifying in vitro the genomic DNA, the single stranded DNA or the oligonucleotide to obtain at least 10 femtomoles of the genomic DNA, the single stranded DNA or the oligonucleotide, whereby to form a template,
  (b) aliquoting the resultant template from (a) into two aliquots,
  (c) adding to each aliquot from (b) a labeled primer specific for each end of the template,
  (d) subaliquoting each of the two aliquots from (c) into two sets of five aliquots,
  (e) for each set of aliquots from (d), adding a dideoxynucleotide terminator for guanine to one aliquot, adding a dideoxynucleotide terminator for adenine to one aliquot, adding a dideoxynucleotide terminator for cytosine to one aliquot and adding a dideoxynucleotide terminator for thymine to one aliquot and maintaining one aliquot as a control,
  (f) thermally cycling each of the aliquots from (e), and
  (g) separating out the resultant molecules according to size.

The present invention concerns a method for detecting a genetic disease (for example, sickle cell anemia) or a tumor which involves a base pair mutation comprising (a) amplifying in vitro with two locus specific primers, a genomic DNA from a patient, e.g., a human patient, to obtain at least 10 femtomoles of the genomic DNA whereby to form a template,
(b) synthesizing simultaneously truncated strands from both ends of the template by introducing a dideoxynucleotide terminator for each of the four bases adenine, guanine, cytosine and thymine and introducing a label or labels specific for either or both of the 5' ends of the synthesized strands,
(c) thermally cycling step (b) to provide a sufficiently readable signal,
(d) separating out the resultant molecules according to size and
(e) determining the presence of a base pair mutation as an indication of a genetic disease or tumor.

The present invention also relates to a method for identifying an individual (i.e., human), an animal or a plant from a genomic DNA sample of the individual, animal or plant comprising (a) amplifying in vitro with two primers for each sample, the primers being specific for a polymorphic locus, two genomic DNA samples, one of the samples from the individual, animal or plant and the other sample suspected to be from the individual, animal or plant to obtain at least 10 femtomoles of the genomic DNA for each sample, whereby to form a template for each sample DNA,
(b) synthesizing simultaneously truncated strands from both ends of each template by introducing a dideoxynucleotide terminator for each of the four bases adenine, guanine, cytosine and thymine and introducing a label or labels specific for either or both of the 5' ends of the synthesized strands,
(c) thermally cycling step (b) to provide a sufficiently readable signal for each sample,
(d) separating out the resultant molecules according to size for each sample and
(e) comparing the results from step (d) for each sample to determine a pattern of polymorphic bases as an indication of identity.

The above identification method can be utilized in forensics and law enforcement. For example, a semen, urine, blood or hair sample at a crime scene can be compared to a DNA sample taken from a suspect. Another use of such identification method would be to identify animals in zoos and wildlife populations. For example, a DNA sample from an animal can be stored and then later compared to a sample from the animal.

With respect to the above identification method, once a polymorphism has been identified with a breed of animal or a variety of plant, the present invention can be utilized to identify a given animal or plant as being associated with such breed or variety.

The present invention is also directed to a method to determine paternity comprising (i) conducting the following steps on a genomic DNA sample for each of a mother, a suspected father and a child of the mother:

(a) amplifying in vitro with two primers specific for a polymorphic locus the genomic DNA to obtain at least 10 femtomoles of the genomic DNA whereby to form a template,
(b) synthesizing simultaneously truncated strands from both ends of the template by introducing a dideoxynucleotide terminator for each of the four bases adenine, guanine, cytosine and thymine and introducing a label or labels specific for either or both of the 5' ends of the synthesized strands,
(c) thermally cycling step (b) to provide a sufficiently readable signal and
(d) separating out the resultant molecules according to size and (ii) comparing the results from all three samples to detect if the child's DNA sample has base pairs from both the father and the mother in a polymorphic position.

The present invention also concerns a method for detecting a bacterial or viral infection and/or detecting a bacterial or viral strain comprising (a) amplifying in vitro with two bacterial or viral specific primers, a DNA sample from a patient, e.g., a human, suspected of containing bacteria or virus to obtain at least 10 femtomoles of the DNA whereby to form a template,
(b) synthesizing simultaneously truncated strands from both ends of the template by introducing a dideoxynucleotide terminator for each of the four bases adenine, guanine, cytosine and thymine and introducing a label or labels specific for either or both of the 5' ends of the synthesized strands of the bacterial or viral DNA,
(c) thermally cycling step (b) to provide a sufficiently readable signal,
(d) separating out the resultant molecules according to size and
(e) determining the presence or absence of a bacterial or viral DNA sequence or specific base pairs which identify a bacterial or viral strain. If there is a gel band, the bacteria or virus is present. If there is no gel band, a bacterial or viral infection is not present.

The above described methods for detecting a genetic disease or a tumor, identifying paternity and detecting bacterial or viral infection or strains can also be carried out by the above described aliquot process.

The present invention further relates to an apparatus for sequencing DNA or oligonucleotides comprising (a) a means to conduct thermal cycling, for example, comprising heating resistors and refrigeration units as used in the PCR process,
(b) a means to aliquot dideoxynucleotide terminators, for example, automatic arms that move back and forth to dispense dideoxynucleotide terminators in specific amounts,
(c) a means to resolve molecules on the basis of size, for example, chromatography, and
(d) a means of scanning molecules for the presence of labels, for example, a means to detect fluorescent dyes by examining wavelengths of light.

BRIEF DESCRIPTION OF THE DRAWINGS

FIG. 1 illustrates an autoradiograph of a polyacrylamide sequencing gel for a 300 bp subfragment within a Pst I fragment 4 kb upstream from human HOX 2.2 in chromosome 17. The gel illustrates two sequencing ladders, one from primer Pyg2 (FIG. 1a and FIG. 1b) and another from Pyg3 (FIG. 1c and FIG. 1d). The sequencing ladders are complementary, since they extend from opposite ends of the same fragment. Two sets of reactions are,depicted for each primer. One ladder is a "short run" (FIG. 1b; FIG. 1d), i.e., electrophoresis of products for 2.5 hours. The "long run" (FIG. 1a; FIG. 1c) corresponds to the same products electrophored for a longer time (5 hours) from an earlier load. The arrows delimit a 15 base track clearly readable from both ends for confirmation of complementary sequence. The sequences are written to the left of each ladder.

FIG. 2 illustrates four close-ups of relevant portions of an autoradiograph of a polyacrylamide sequencing gel documenting two base pair changes (polymorphisms) between two different chimpanzees (designated "COLIN" and "109"). The fragment, amplified from genomic DNA with the same human primers Pyg2 (FIG. 2*a*; 2*b*) and Pyg3(FIG. 2*c*; FIG. 2*d*) above, is 300 bp in length and corresponds to a region in a homeo box gene cluster homologous to that depicted for a human in FIG. 1. The fragment is sequenced from both ends using primer Pyg2 to sequence one strand and primer Pyg3 to sequence the other. Arrows indicate the sequence changes.

DETAILED DESCRIPTION OF THE INVENTION

One embodiment of the present invention couples amplification of a defined genomic segment, or a single stranded DNA or an oligonucleotide via the polymerase chain reaction with DNA sequencing via dideoxynucleotide chain termination. Such embodiment can be termed "coupled amplification and sequencing" or "CAS".

The above described process is biphasic. In Stage I, a modified version of the polymerase chain reaction allows 10,000 to 100,000-fold amplification of a genomic segment of 1 kb or less starting from μg amounts of genomic DNA. At the beginning of Stage II, 8 of 10 identical aliquots of Stage I product are set aside. Each aliquot receives one of the 4 dideoxynucleotides and a radiolabelled supplement of one of the two PCR primers. Hence five sequencing reactions from each end of the PCR fragment are set in the array of ten aliquots (two are controls). These ten sequencing reactions are thermally cycled during Stage II to simultaneously amplify both the template and the truncated products giving rise to two sequencing ladders on a polyacrylamide gel. The sequencing ladders are complementary, since each starts at opposite 5' ends of the PCR fragment. Concentrations of deoxynucleotides, of dideoxynucleotides and of PCR primers are optimized empirically for the process.

The above described proces allows for the template generated in Stage I to be sequenced with the same buffer and enzyme that synthesized it. No purification is required.

The above described process allows for both strands of a genomic DNA segment of interest to be sequenced in a single experiment for instantaneous confirmation of sequence and clarification of uncertain areas in a given strand.

The above described process allows for sequencing reactions to be repeated via multiple rounds (cycles) of denaturation, primer annealing and polymerization. Simultaneously, the template is also being amplified, thus further enhancing the signal.

As an alternate to PCR as an amplification procedure, a ligation directed assay (Abbott Laboratories) can be employed.

Oligonucleotide ligation assays for mutations could be checked for accuracy by sequencing the ligation product (Landegren et al, (1988), *Science*, 241, 1077).

Figure 5:
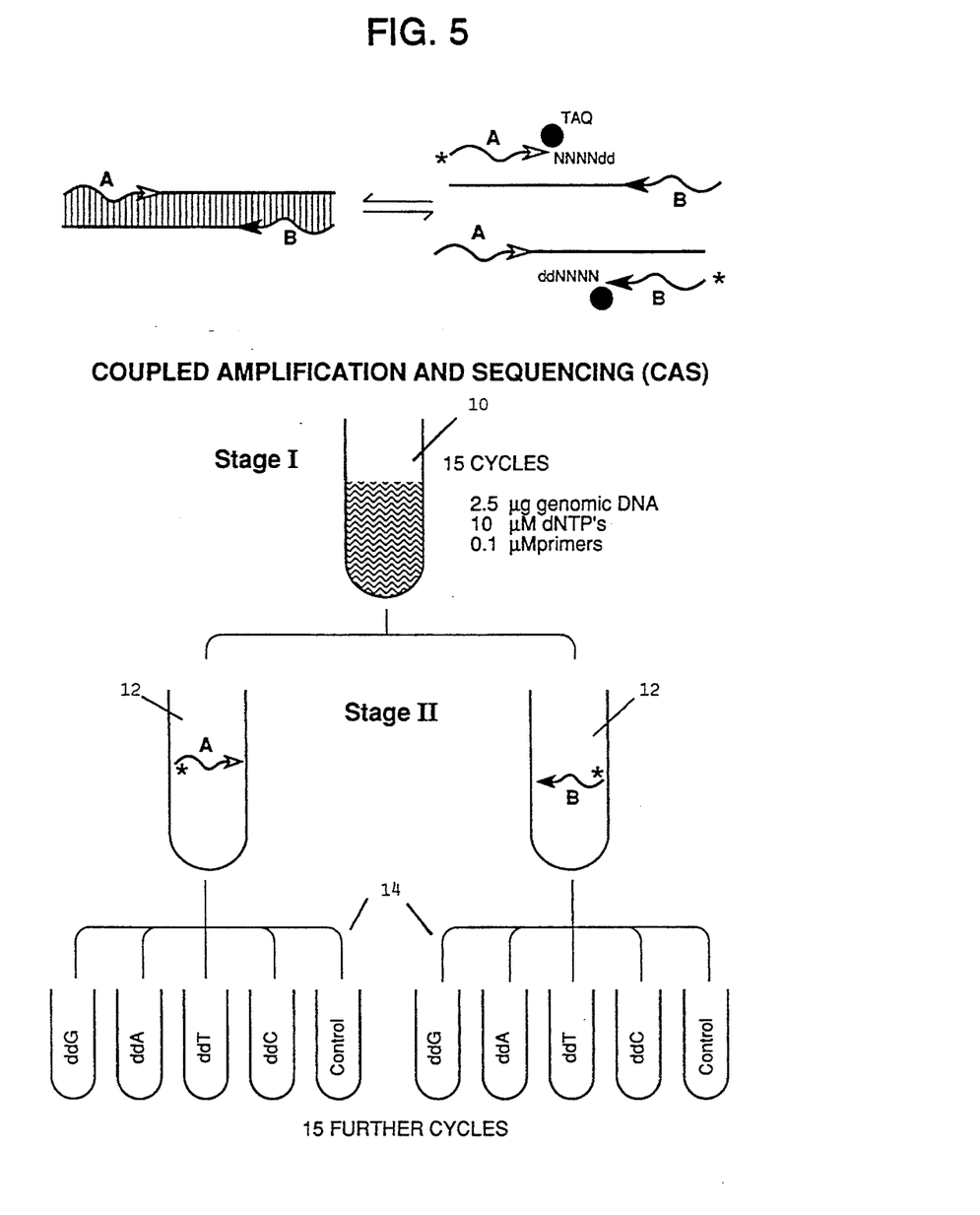
FIG. 5 is a schematic representation of an embodiment of a process according to the invention.

FIG. 5 depicts an embodiment of the present invention. In test tube 10 is contained 250 μl of a genomic DNA which is amplified using a buffer containing a thermally stable enzyme, e.g., Taq polymerase enzyme, preferably highly purified, deoxynucleotides (dNTPs) salts, e.g., KCl and $MgCl_2$ and Tris. The amplification involves a series of cycling steps ("thermal cycling") including denaturation at 90° to 95° C., preferably 94° C., annealing at 45° C. to 65° C. (the temperature depends on the target), preferably 57° C., and extension at 65° C. to 75° C., preferably 72° C.

In the annealing step, the primer binds (hydrogen bonding) to the template at a specific site. In the extension step, the polymerase enzyme finds the primer-target complex and makes a copy of the template incorporating the primer in the synthesized strand. In denaturation, the resulting double stranded product of the extension reaction (polymerization reaction) is "boiled", i.e., denatured, to separate the strands.

The number of cycles conducted in the first stage in tube 10 is fifteen to twenty five and preferably fifteen cycles.

The amplified material (template) from tube 10 is split into two aliquots 12. To each aliquot 12, a labelled primer for each end is added (A' and B'). The label can be a radioactive moiety, a dye or a fluorescent moiety, just to name a few.

Aliquots 12 are subaliquoted into two sets of five aliquots each 14. To one aliquot in each of the two sets is added a terminator for G, A, T and C. One aliquot of each set acts as a control.

Each of the aliquots 14 are thermally cycled as described above for ten to twenty cycles, preferably fifteen cycles.

The molar ratios of the dideoxy (dideoxynucleotide) terminators (ddG, ddA, ddC and ddT) to the deoxy (deoxynucleotide) elongators (dG, dA, dC and dT) are as follows:

$$\frac{ddG}{dG} = 8 \text{ to } 14, \text{ preferably } 10,$$

$$\frac{ddC}{dC} = 40 \text{ to } 60, \text{ preferably } 40,$$

$$\frac{ddA}{dA} = 60 \text{ to } 100, \text{ preferably } 64,$$

and $$\frac{ddT}{dT} = 60 \text{ to } 100, \text{ preferably } 64.$$

Alternatively, 7-deaza-2'-deoxyguanosine triphosphate can be employed in place of dG. Furthermore, deoxyinosine triphosphate can be utilized in place of dC, dT, dG or dA.

The deoxy elongators are preferably maintained at 10 micromolar.

In Stage II, the molar ratio of labelled primer to unlabelled primer is 0.5 to 5.0, preferably 1. In Stage II, 10 picomoles, for example, of labelled primer is introduced.

Applicant employs a modified version of PCR in that reduced amounts of deoxynucleotides (e.g., 10 micromolar) and unlabelled primers (e.g., 0.1 micromolar) are employed.

The aliquoting procedures described above can be dispensed with if different "specific" labels are employed for A' and B', i.e., specific labels for each of the 5' ends of the synthesized strands.

The amount of enzyme employed is generally 2 units, e.g., 0.1 picomoles, of for example, Taq polymerase.

The product from Stage II is subject to a separating out of the resultant molecules according to size. Preferably this separating out is conducted by high resolution gel electrophoresis.

Labels for use in the present invention include, substances which have a detectable physical, chemical, or electrical property. When a detectable labeling substance is introduced, it can be linked directly such as by covalent bonds or can be linked indirectly such as by incorporation of the ultimately detectable substance in a microcapsule or liposome.

Labeling materials have been well-developed in the field of immunoassays and in general almost any label useful in such methods can be applied to the present invention. Particularly useful are enzymatically active groups, such as enzymes (see *Clin. Chem.*, (1976) 22:1232, U.S. Pat. No. Re. 31,006, and UK Pat. 2,019,408), enzyme substrates (see U.S. Pat. No. 4,492,751), coenzymes (see U.S. Pat. Nos. 4,230,797 and 4,238,565), and enzyme inhibitors (see U.S. Pat. No. 4,134,792); fluorescers (see *Clin. Chem.*, (1979) 25:353); chromophores; luminescers such as chemiluminescers and bioluminescers (see U.S. Pat. No. 4,380,580); specifically bindable ligands such as biotin (see European Pat. Spec. 63,879) or a hapten (see PCT Publ. 83-2286); and radioisotopes such as $^3H$ $^{35}S$, $^{32}P$, $^{125}I$ and $^{14}C$. Such labels are detected on the basis of their own physical properties (e.g., fluorescers, chromophores and radioisotopes) or their reactive or binding properties (e.g., ligands, enzymes, substrates, coenzymes and inhibitors). For example, a cofactor-labeled species can be detected by adding the enzyme (or enzyme where a cycling system is used) for which the label is a cofactor and a substrate or substrates for the enzyme. A hapten or ligand (e.g., biotin) labeled species can be detected by adding an antibody to the hapten or a protein (e.g., avidin) which binds the ligand, tagged with a detectable molecule. Such detectable molecule can be some molecule with a measurable physical property (e.g., fluorescence or absorbance ) or a participant in an enzyme reaction (e.g., see above list). For example, one can use an enzyme which acts upon a substrate to generate a product with a measurable physical property. Examples of the latter include, but are not limited to, beta-galactosidase, alkaline phosphatase and peroxidase.

Methods for preparing a labeled primer used in a preferred embodiment of the present invention are readily available from the prior art. When labeling, one will employ synthetic approaches which are effective for modifying nucleic acids without substantially interfering with the ability of the labeled primers to participate in hybridization and extension, and will select labels which are sufficiently stable under the conditions to be used for extension and subsequent detection. For methods on agglutination detection see Grieco and Meriney, *Immunodiagnosis for Clinicians* (1983), Chapter 2.

The present invention also encompasses kits for conducting the aforementioned processes. Such kits include in one or more containers, a set of instructions, and one or more of a thermally stable enzyme, e.g., Taq polymerase, salts, e.g., KCl and $MgCl_2$, Tris, deoxynucleotides for each of adenine (A), guanine (G), cytosine (C) and thymine (T), dideoxynucleotides for each of adenine (A), guanine (G), cytosine (C) and thymine (T) and labelled primers.

The present invention has many applications in clinical diagnosis and genetic research fields, which have been revolutionized by the polymerase chain reaction.

PCR has increased the reliability, feasibility and speed of molecular diagnosis of genetic disease. Invariably, PCR products are analyzed for sequence variation via restriction fragment length polymorphisms, allele specific oligonucleotides or denaturing gradient electrophoresis. All along it has been appreciated, however, that sequencing of these products is the ultimate level of resolution for diagnostic analysis. Unfortunately, technical difficulties have made this goal unattainable. The present invention overcomes these obstacles and renders feasible the routine diagnosis of genetic disease on the basis of actual DNA sequence.

In a research context, the current effort to map and eventually sequence the human genome is increasingly based on PCR technology. A recent proposal has advocated the creation of chromosomal milestones defined by genomic segments or "sequence tagged sites" (STS) (Olson et al, *Science,* 245:1434, (1989)). Each segment is delimited by a pair of flanking PCR primers in order to allow any laboratory in the world to abstract the same product from the genome via PCR. The present invention could become indispensable for corroborating the fidelity of the amplified STS, as well as for assaying polymorphisms in human populations. The inventive process will also provide a convenient means of sequencing products generated via the multiple modifications of PCR which yield genomic segments of unknown sequence (inverse PCR, Alu PCR, PCR with degenerate primers, cross species PCR, anchored PCR, etc.).

One of the main thrusts of research on genome analysis is automation of its many technical aspects. The present invention is particularly suited to automation. The PCR process is already automated for the amplification phase. The sequence analysis of amplified products via the present invention fits in well with the existing technology.

Coupled amplification and sequencing according to the invention requires neither preparative steps for template, nor nested primers for sequencing. A single experiment can yield sequences for both complementary strands. Multiple original copies of template (300,000 in 1 $\mu$g genomic DNA) enhance sequence fidelity. This method is tailored for sequencing of short segments ($\approx$400 bp) screened for human polymorphism and for inter-species variation by denaturing gradient electrophoresis. As mentioned above, these methodologies are being developed as a general paradigm for linking STS's to the genetic map and for evolutionary studies of defined genomic segments.

Several of the above described methods of the present invention involve the use of specific primers. Specific primers flank a defined site in the genome. Such site is defined herein as a locus. The locus flanked by the primers is amplified and sequenced, i.e., its base pair sequence is determined by the invention. In the case of a mutation, the locus is the location where the mutation occurs. In the case of a tumor, the locus is where the disease tissue has a base pair change rendering it cancerous. In case of identification, the locus is a polymorphic segment in a genome known to be variable in a human population, an animal population or a plant population. In the case of virus and bacteria, the locus is defined as the bacterial or viral DNA that has invaded the host cells. A strain specific locus is defined as a DNA segment variable in the bacterial or viral population which allows it to be identified as a specific strain.

Non-limiting examples of primers for use in the present invention include the following:

Purpose: Diagnosis of AIDS, a viral infectious disease

Primer sequences (5' to 3') and [nomenclature for primer, i.e. name]

ATA ATC CAC CTA TCC CAG TAG GAG AAA T [SK38]
TTT GGT CCT TGT CTT ATG TCC AGA AAT GC [SK39]

Reference: Ou et at 1988, Science 238: 295-297
Purpose: Diagnosis of sickle cell anemia, a genetic disease Primer sequences (5' to 3') and [nomenclature for primer, i.e. name]

ACA CAA CTG TGT TCA CTA GC [PC03]
CAA CTT CAT CCA CGT TCA CC [PC04]

Reference: Saiki et al 1986, Nature 324: 163-166
Purpose: individual identification by amplification of a polymorphic locus (polymorphic locus is HLA DQ$_a$)

Primer sequences (5' to 3') and [nomenclature for primer, i.e. name]

GTG CTG CAG GTG TAA ACT TGT ACC AG [HG26]
CAC GGA TCC GGT AGC AGC GGT AGA GTT G [GH26]

Reference: Erlich and Bugawan 1990, *PCR Protocols*, Academic Press, pp 261-271.

The invention will now be described with reference to the following non-limiting examples.

Example 1

During the exponential phase of PCR, simultaneous primer extensions occur on most template molecules generated in previous cycles. During this phase it is possible to introduce dideoxynucleotides and an end-labelled aliquot of one of the primers as tracer without impairment of extension by strand reannealing. The biphasic "booster" logic developed for PCR of dilute DNA samples (Ruano et al, 1989, NAR, 17:5407) was applied to the coupled amplification and sequencing of both strands of a "Sequence Tagged Site" (STS) of known sequence in human homeo box cluster 2 (Ruano et al, 1990, *Nucleic Acids Res.*, 18:1314).

Stage I consists of 15 cycles during which human genomic DNA (1 μg) is amplified under standard conditions (50 mM KCl 10 mM Tris pH 8.4, 1.5 mM MgCl$_2$, 2U Taq polymerase, 100 μl reaction volume), but with reduced amounts of deoxynucleotides (10 μM each) and primers 0.1 μM). At the beginning of Stage II, each dideoxynucleotide is aliquoted into 2 PCR tubes. Concentration of either PCR primer is boosted in separate tubes for each dideoxy with 10 picomoles of primer end-labelled at 2-4 μCi/picmole. The reactions then undergo 15 further cycles with the same thermal profile as in Stage I.

The dideoxynucleotide concentrations ["dd"] required for chain termination were titrated by examining the range from 0 to 1000 μM for each dideoxy. There was an inverse relationship between [dd] and yield of full-length PCR product. Truncated products were present even at [dd] of 0, thus evidencing the occurrence of multiple stops by Taq polymerase during regular PCR (Olsen and Eckstein, 1989, *Nucleic Acid Res.*, 17:9613). As [dd] increased, the random stops were reduced and the truncated products coalesced into a sequencing ladder with negligible background signal. The didexoy to deoxy ratios at which the ladders became readable corresponded with almost undetectable yields of full PCR product. The optimal ratio was specific to each dideoxy; 64 for ddA and ddT, 40 for ddC, 10 for ddG (final optimal concentrations: 10μM each deoxynucleotide, 640 μM ddA, 640 μM ddT, 400 μM ddC, 100 μM ddG). These ratios are two-fold higher than reported for linear extension on single stranded templates by Taq polymerase [Innis et al, 1989, *Proc. Natl. Acad. Sci. USA*, 85:9436]. Electrophoresis of 10% of the product in high resolution acrylamide gels resulted in ladders readable after overnight exposures without intensifying screens.

Example 2

The human homeo box cluster 2 (HOX2) contains genes coding for DNA binding proteins involved in developmental control and is highly conserved between mouse and man (Schughart et al, 1988, *Br. J. Cancer*, 58 (Suppl IX): 9). CAS has been applied to sequence defined primate HOX2 segments and to detect sequence differences among them. If priming sites are conserved, homologous PCR products can be amplified from primate genomes via Cross-Species PCR (CS-PCR) using human primers (Ruano et al, 1989, *J Cell Biochem*, 13E: 303).

A Pst I fragment 4 kb upstream from human HOX 2.2 has been cloned and sequenced by classical methods (Ferguson-Smith, 1989, PhD Thesis, Yale University). From this sequence, primers delimiting a 300 bp subfragment within the Pst I fragment have been synthesized and utilized to amplify the subfragment directly from genomic DNA (Ruano et al, 1990, *Nucleic Acids Research*, 18: 1314). Such primers are Pyg2 [5'-GCTCTATAGGAGGCCCTGAG-3'] and Pyg3 [5'-GAGGCTGTTTAGATGAGACA-3'].

This fragment was sequenced with CAS and corroborated with data from Ferguson-Smith [op. cit.]. The sequencing ladder extended from primers Pyg2 and Pyg3 corresponding to both complementary strands of the fragment is shown in FIG. 1. The sequence obtained with CAS perfectly matches that obtained by classical means.

One of the virtues of CAS is instant confirmation of sequence by ladders extending from both primers. In FIG. 1, a track of 15 bases has been highlighted for this purpose. From Pyg3, proceeding from bottom to top of the short gel ("Pyg3 short"), the sequence reads 5'-GAT CTT TAG GGG AGT -3'. From Pyg2, the track electrophoresed for 5 hours, "Pyg2 long", reads 5'-ACT CCC CTA AAG ATC-3'. Aligning both sequences in an antiparallel configuration it can be seen that they are perfectly complementary, which allows their confirmation:

5'-GAT CTT TAG GGG AGT-3'

3'-CTA GAA ATC CCC TCA-5'.

Methods: Stage I and II of CAS consisted of 15 cycles each [1' at 94° C.; 1' at 57° C.; 1' at 72° C.]. Stage I: 0.1 μM primers, 10 μM dNTPs, 2.5 μg genomic DNA, 250 μl total reaction volume. Stage II: reaction mixture from stage I is aliquoted into two identical volumes. Concentration of either PCR primer is boosted in these separate tubes with 10 picomoles of primer end-labelled at 2-4 μCi/picomole. Each mixture containing end-labelled primer and Stage I products is subaliquoted into 5 tubes, one for each dideoxynucleotide and one serving as a control without any dideoxynucleotide. Final concentrations for Stage II: 10 μM each deoxynucleotide, 640 μM ddA, 640 μM ddT, 400 μM ddC, 100 μM ddG. The reactions then underwent 15 further cycles with the same thermal profile as in Stage I. Electrophoresis of 10% of product in high resolution acrylamide gels resulted in ladders readable after overnight exposures without intensifying screens.

Example 3

One of the most potentially useful features of CAS is the capability for surveying populations of organisms for genetic variation. Previous methods of classical cloning would have required libraries of each organism to be screened, relevant clones isolated and grown and finally subcloning of relevant pieces for sequence analysis. CAS obviates all these steps, as a given pair of PCR primers could be used for amplification and sequencing directly from whole genomic DNA extracted from each organism.

Figure 1A:
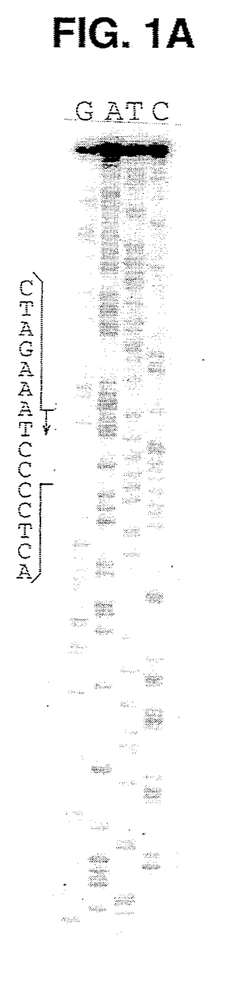
Figure 1B:
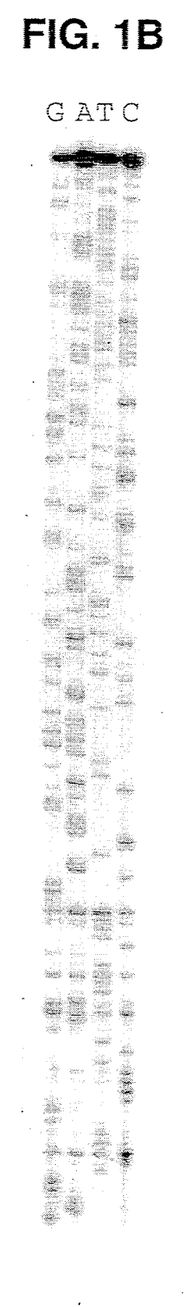
Figure 1C:
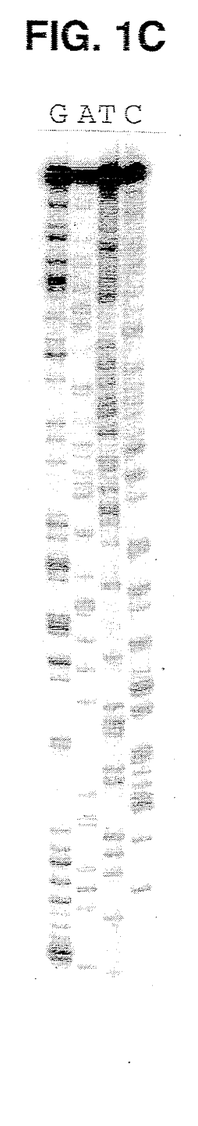
Figure 1D:
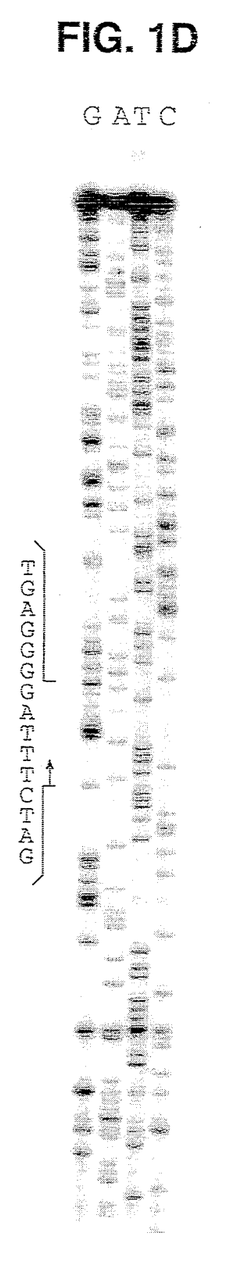
Figure 2A:
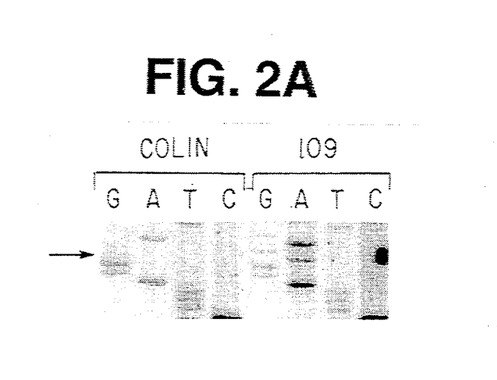
Figure 2B:
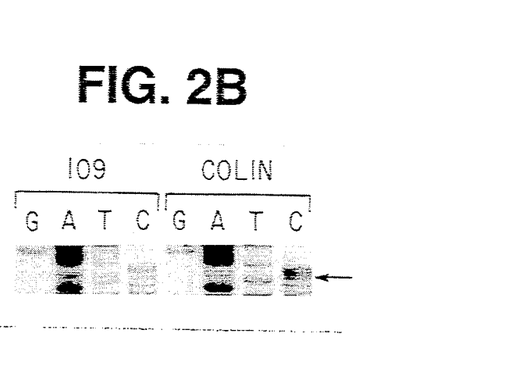

In this example, genomic DNA from two chimpanzees, Colin and 109, were sequenced via CAS for a highly conserved segment in a homeo box cluster. Two base pairs were found to be polymorphic in these animals as illustrated in FIG. 1 and FIG. 2. In FIG. 2a, the sequence extended from primer Pyg 3 is CTT TAG GGG AGT for COLIN and CTT TAG GAG AGT for 109. FIG. 2b presents the complementary sequence, obtained from primer Pyg 2 extension: ACT CCC CTA AAG for COLIN and ACT CTC CTA AAG for 109. The polymorphic base is underlined. CAS allows confirmation of the polymorphism from both ends of the molecule.

Figure 2C:
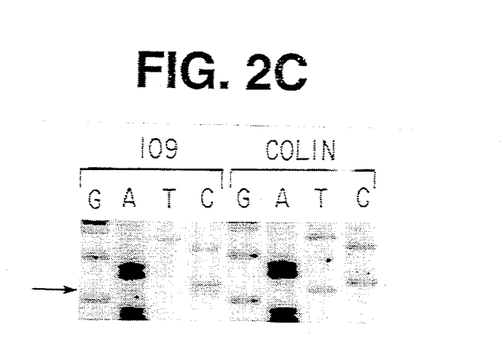
Figure 2D:
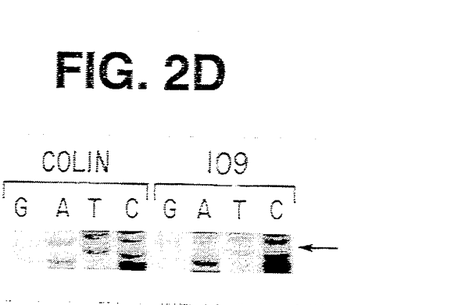

A similar analysis for the other polymorphism is presented in FIG. 2c and FIG. 2d of FIG. 2. In FIG. 2c, the sequence extended from primer Pyg2 reads AAG CCA AGC TGG for 109 and AAG TCA AGC TGG for COLIN. In FIG. 2d, complementary sequence extending from primer Pyg3 reads CCA GCT TGG CTT for 109 and CCA GCT TGA CTT for COLIN. Again the polymorphism is confirmed by reading from both ends sequence generated in a single CAS experiment.

Example 4

Optimization of the CAS process required careful titration of dideoxynucleotide concentrations. It is well known in the art of DNA sequencing that high dideoxynucleotide amounts may lead to very short strands extended from the primer with consequent loss of sequence data from segments distal to the primer. Conversely, very low amounts may lead to long strands extended from a given primer with consequent loss of sequence information from sites proximal to the primer. In the case of CAS these issues were complicated by the presence of many "natural" stops of Taq polymerase during regular PCR. The noise had to be filtered in order to obtain clear sequencing ladders. A further issue exclusive to CAS is the requirement for some strands to make it through to the other end of the fragment in order to sustain some degree of amplification.

Figure 3:
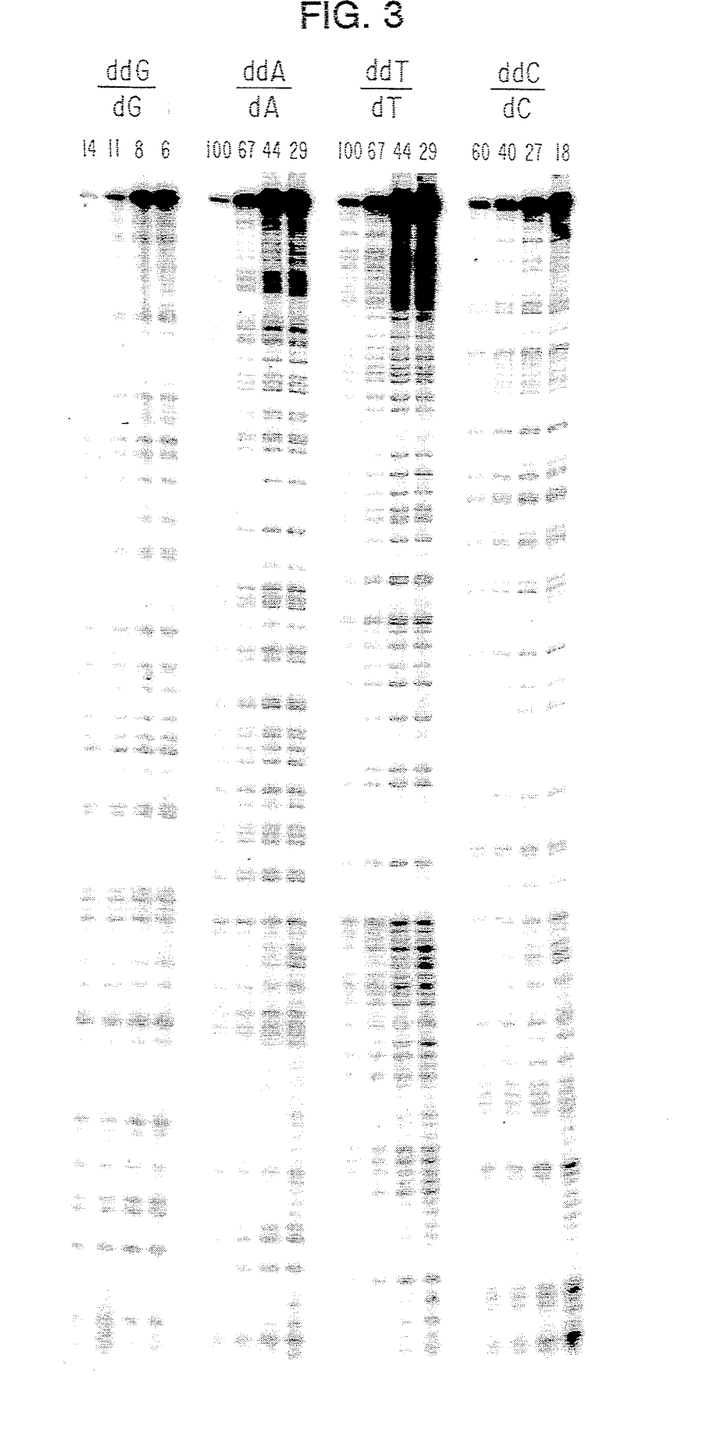
FIG. 3 illustrates an autoradiograph of a polyacrylamide gel demonstrating a titration series to optimize the ratio of the terminator (dideoxynucleotide) to the elongator (deoxynucleotide) of all four bases (G, A, T and C) for a 300 bp fragment in human homeo box cluster 2.
Figure 4:
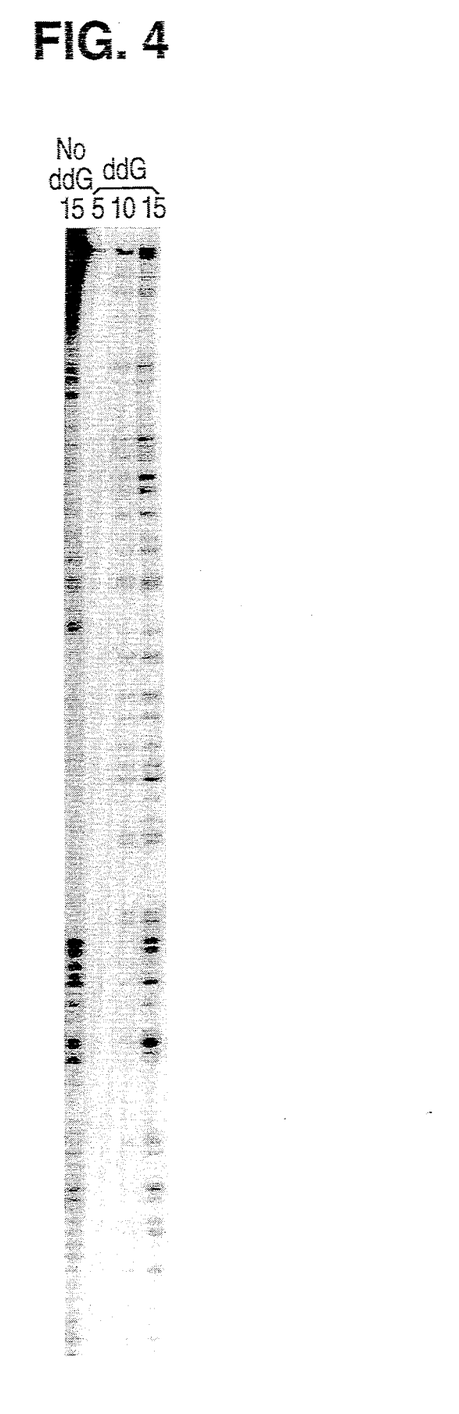
FIG. 4 illustrates an autoradiograph of a sequencing ladder for G after 5, 10 and 15 cycles of Stage II (i.e., after addition of ddG and end-labelled primer). This gel illustrates the optimization of the number of Stage II cycles.

In order to examine the effects of dideoxynucleotide concentration in the physical chemistry of CAS, an extensive titration series was performed and is illustrated in FIG. 3. The concentration of deoxynucleotides (dG, dA, dT, dC) was 10 μM in all experiments during Stages I and II. During Stage II, a variable amount of dideoxynmucleotides was added to each tube, over a range in accordance with the known Km's of Taq polymerase for ddNTP incorporation. For ddG, the range extended from 60 to 140 μM; for ddA and for ddT, from 290 to 1000 μM; and for ddC, from 180 to 600 μM. The corresponding ratios of dideoxynucleotide to deoxynucleotide thus range from 6 to 14 for ddG, from 29 to 100 for ddA and ddT, and from 18 to 60 for ddC.

In all four titration series, increasing amounts of ddNTP reduced the background noise of the process to undetectable levels without impairment in the clarity and strength of the signal obtained from the bona fide sequencing ladder. Thus the signal to noise ratio for this system was increased selectively at the optimum dd/d ratio. Strikingly, the intensity of low molecular weight and high molecular weight bands is uniform at any given dideoxy amount. Considerable full-length product was observed at all dideoxymucleotide concentrations, but its yield was inversely related to dd/d ratio. The strength of the signal decreased at dd/d ratios beyond the optimum. Optimal dd/d ratios determined from this series are: 11 for G, 67 for A and for T, 40 for C.

It will be appreciated that the instant specification is set forth by way of illustration and not limitation, and that various modifications and changes may be made without departing from the spirit and scope of the present invention.

What is claimed is:

1. A process for sequencing DNA segments comprising:
   (a) exponentially and simultaneously synthesizing both truncated products and full length products starting from 3' ends of each of two complementary strands of the DNA segment which serve as a template, Said exponential and simultaneous synthesis using the following reagents:
      (i) a first primer for annealing to the 3' end of one of said two complementary strands of the DNA segment,
      (ii) a second primer, which is different from the first primer, for annealing to the 3' end of the other of said two complementary strands of the DNA segment,
      (iii) a reaction buffer,
      (iv) a deoxyribonucleotide elongator for each of adenine, guanine, cytosine and thymine,
      (v) a thermally stable DNA polymerase and
      (vi) a dideoxynucleotide terminator for each of adenine, guanine, cytosine and thymine, carrying out said synthesis by thermal cycling to provide a sufficiently readable signal, separating out the resultant truncated products and full length products according to size, and selectively detecting truncated products and full length products synthesized from one or the other of said two complementary strands of the DNA segments.

2. A process according to claim 1, wherein the thermally stable DNA polymerase is Taq DNA polymerase.

3. A process according to claim 1, wherein said thermal cycling comprises 10 to 20 cycles of denaturation at 90° to 95° C., annealing at 45° to 65° C. and extension at 65° to 75° C.

4. A process according to claim 1, wherein the separating out is conducted by high resolution gel electrophoresis.

5. A process according to claim 1, wherein the molar ratio of the dideoxynucleotide terminators the deoxyribonucleotide elongators are as follows:

$$\frac{ddG}{dG} = 8 \text{ to about } 14,$$

$$\frac{ddC}{dC} = 40 \text{ to about } 60,$$

$$\frac{ddA}{dA} = 60 \text{ to about } 100,$$

and $$\frac{ddT}{dT} = 60 \text{ to about } 100.$$

6. A process for determining a base sequence of a DNA segment comprising (a) amplifying in vitro said DNA, to obtain at least 10 femtomoles of amplification products, to form a template, (b) aliquoting the resultant template from (a) into two aliquots, (c) adding to each aliquot from (b) a labeled primer specific for each end of the template, (d) subaliquoting each of the two aliquots from (c) into two sets of five aliquots, (e) for each set of aliquots from (d), adding a dideoxynucleotide terminator for guanine to one aliquot, adding a dideoxynucleotide terminator for adenine to one aliquot, adding a dideoxynucleotide terminator for cytosine to one aliquot and adding a dideoxynucleotide terminator for thymine to one aliquot and maintaining one aliquot as a control, (f) thermally cycling each of the aliquots from (e), and (g) separating out the resultant molecules according to size and selectively detecting products synthesized from one or the other of said strands of said amplification products to determine the sequence.

7. A process according to claim 6, wherein said amplifying comprises introducing a thermally stable enzyme, salts and a deoxyribonucleotide elongator for each of adenine, guanine, cytosine, and thymine and conducting 15 to 25 cycles of denaturation at 90° to 95° C. annealing at 45° to 65° C. and extension at 65° to 75° C.

8. A process according to claim 6, wherein the molar ratios of the dideoxynucleotide terminators to the deoxyribonucleotide elongators are as follows:

$$\frac{ddG}{dG} = 8 \text{ to about } 14,$$

$$\frac{ddC}{dC} = 40 \text{ to about } 60,$$

$$\frac{ddA}{dA} = 60 \text{ to about } 100,$$

and $$\frac{ddT}{dT} = 60 \text{ to about } 100.$$

9. A process according to claim 6, wherein thermal cycling is carried out with Taq DNA polymerase.

10. A process according to claim 6, wherein the separating out is conducted by high resolution gel electrophoresis.

11. A process according to claim 1, wherein the DNA segment is a genomic DNA fragment of less than 2 kb.

12. A process according to claim 11, wherein the DNA is amplified in vitro to form said template.

13. A process according to claim 12, wherein the DNA polymerase is Taq DNA polymerase; the thermally cycling comprises 10 to 20 cycles of denaturation at 90° to 95° C., annealing at 45° to 65° C. and extension at 65° to 75° C.; the amplifying comprising introducing a thermally stable Taq DNA polymerase enzyme, salts and a deoxyribonucleotide elongator for each of adenine, guanine, cytosine and thymine and conducting 15 to 25 cycles of denaturation at 90° to 95° C., annealing at 45° to 65° C. and extension at 65° to 75° C.; the separating out is conducted by high resolution gel electrophoresis; and the molar ratios of the dideoxynucleotide terminators to the deoxyribonucleotide elongators are as follows:

$$\frac{ddG}{dG} = 8 \text{ to about } 14,$$

$$\frac{ddC}{dC} = 40 \text{ to about } 60,$$

$$\frac{ddA}{dA} = 60 \text{ to about } 100,$$

and $$\frac{ddT}{dT} = 60 \text{ to about } 100.$$

14. A process according to claim 7, wherein the amplification using thermally stable Taq DNA polymerase enzyme, salts and a deoxyribonucleotide elongator for each of adenine, guanine, cytosine and thymine and conducting 15 to 25 cycles of denaturation at 90° to 95° C., annealing at 45° to 65° C. and extension at 65° to 75° C.; the separating out is conducted by high resolution gel electrophoresis; and the molar ratios of the dideoxynucleotide terminators to the deoxyribonucleotide elongators are as follows:

$$\frac{ddG}{dG} = 8 \text{ to about } 14,$$

$$\frac{ddC}{dC} = 40 \text{ to about } 60,$$

$$\frac{ddA}{dA} = 60 \text{ to about } 100,$$

-continued and $$\frac{ddT}{dT} = 60 \text{ to about } 100.$$

15. The process according to claim 1 wherein the detection is accomplished by using a labeled primer as said first or second primer.

16. The process according to claim 1 wherein detection is accomplished by using differentially labelled primers for both said first and second primers.

17. A process according to claim 6 wherein the DNA segment is a genomic DNA fragment of less than 2 kb.

18. A process according to claim 6 wherein the DNA segment is a single stranded DNA of less than 2 kb.

19. A process according to claim 6 wherein the DNA segment is an oligonucleotide of less than 100 nucleotides.

20. A process according to claim 1, wherein the DNA segment is a single stranded DNA of less than 2 kb.

21. A process according to claim 1, wherein the DNA segment is an oligonucleotide of less than 100 nucleotides.

* * * * *